United States Patent [19]

Gradeff et al.

[11] Patent Number: 4,800,072

[45] Date of Patent: Jan. 24, 1989

[54] ANHYDROUS CEROUS NITRATE-AMMONIUM NITRATE COMPLEX AND A PROCESS FOR ITS PREPARATION FROM CERIC AMMONIUM NITRATE

[75] Inventors: Peter S. Gradeff, Pottersville; Fred G. Schreiber, Highland Park, both of N.J.

[73] Assignee: Rhone Poulenc, Inc., Monmouth Junction, N.J.

[21] Appl. No.: 143,978

[22] Filed: Jan. 14, 1988

[51] Int. Cl.$^4$ ............................................. C06B 1/04
[52] U.S. Cl. ..................................... 423/396; 423/397
[58] Field of Search ........................ 423/395, 396, 397

[56] References Cited

U.S. PATENT DOCUMENTS

| | | | |
|---|---|---|---|
| 377,701 | 2/1888 | Welsbach | 423/395 |
| 2,166,702 | 7/1939 | Blumenfeld | 423/395 |
| 3,100,683 | 8/1963 | Roberts | 423/395 |
| 4,231,997 | 11/1980 | Pitts | 423/395 |
| 4,489,000 | 12/1984 | Gradeff et al. | 260/429.2 |
| 4,492,655 | 1/1985 | Gradeff et al. | 260/429.2 |

FOREIGN PATENT DOCUMENTS 5581 2/1971 Japan ................................. 423/395

OTHER PUBLICATIONS

Gmelin Handbuch der Chimie, German Version and Translation, p. 293 (date: before 1988).
Communist Chinese Sci. Abstr., Chem. 3(Oct.), 9 (1965), Translation.
Chizhikov et al, Russian Journal of Inorganic Chemistry, pp. 1373–1377, (Nov. 1965).

*Primary Examiner*—John Doll
*Assistant Examiner*—Wayne A. Langel
*Attorney, Agent, or Firm*—Morgan & Finnegan

[57] ABSTRACT

A procedure for preparing anhydrous cerous nitrate ammonium nitrate complex comprising treating dried anhydrous ceric hexanitro ammonium complex (ceric ammonium nitrate) with a reducing agent such as ammonia whereby $Ce^{+4}$ is reduced to $Ce^{+3}$ under anhydrous conditions. The resulting $Ce^{+3}$ species, a complex of $Ce^{+3}$ nitrate and ammonia nitrate, can be used as a source of anhydrous $Ce^{+3}$ ions.

15 Claims, No Drawings

ANHYDROUS CEROUS NITRATE-AMMONIUM NITRATE COMPLEX AND A PROCESS FOR ITS PREPARATION FROM CERIC AMMONIUM NITRATE

BACKGROUND OF THE INVENTION

Modern separation techniques for lanthanides yield these elements primarily as chlorides or nitrates in aqueous solution. They are used to make other derivatives such as carbonates, hydroxides, oxides, etc. They can also be used to make some of the organic derivatives such as high alkyl carboxylates or acetyl acetonates. Anhydrous lanthanide inorganic salts, however, are essential for making alkoxides, Ln-carbon bond derivatives and a host of others, as well as for producing metals by electrolytic and metallothermic processes. Oxides can be made anhydrous but their low solubility and limited reactivity precludes their use in many areas. The halides are the only class of compounds that are being used as a source of anhydrous species suitable for these purposes. The easiest ones to make are the fluorides. They have, however, only limited use in syntheses due to extremely low solubility and reactivity. The most difficult ones to dehydrate are the iodides. The bromides and chlorides present similar degree of difficulty that is less than the iodides, but greater than the fluorides. In view of economic and environmental considerations, the chlorides are the most sought anhydrous lanthanide salts. This includes cerium, the most abundant among the lanthanides.

The halides which separate from their aqueous solutions usually retain 6–7 moles of water. After the unbound water has been removed, most of the bound water can be removed by careful dehydration below 100° C. It is extremely difficult, however, to remove the last mole of water without decomposing the halide.

Dehydration of lanthanon chloride hydrates may be done with HCl gas, but this is a tedious process. Dehydration using ammonium chloride in addition to HCl, and under temperatures of 200°–300° C., has shown better results. Oxides have been reacted with sulfur monochloride and chlorine or sulfur monochloride alone, and thionyl chloride, carbon tetrachloride and phosgene also been used as reagents. The preparation of the most commonly used anhydrous salt of lanthanides, the chloride salt, is not an easy task. (Chem. Rev. 1962 pp. 503–511)

U.S. Pat. No. 4,492,655 to Gradeff and Schreiber discloses the preparation of Cerium(III) cyclopentadienyl derivatives using Ceric Ammonium Nitrate and Na-cyclopentadienyl. Using a nitrate was a departure from conventional routes. Ceric ammonium nitrate had the advantage of being easily obtained in anhydrous form. The process of that invention consists of slowly adding alkali metal cyclopentadienide to a solution of ceric ammonium nitrate to form in sequence mono to tricyclopentadienyl cerium. The overall reaction equation is shown as 2[Ce(NO$_3$)$_4$2NH$_4$NO$_3$]+12NaCp→
2Ce(Cp)$_3$+4CpH+(Cp)$_2$+12NaNO$_3$+4NH$_3$ The "in situ" reduction step is shown to proceed via two possible pathways.

Ce(NO$_3$)$_4$+4NaCp→Ce(Cp)$_4$+4NaNO$_3$

2Ce(CP)$_4$+2CpH→2Ce(Cp)$_3$+Cp$_2$+2CpH

The above "in situ" reaction has utility in cases where reagent is a good reducing agent whereby part of the reagent is consumed in the reduction of Ce$^{+4}$ to Ce$^{+3}$. In cases such as the above referred one, this can be rather expensive.

The purpose of this invention is to provide an anhydrous Cerium(III) species that can be used for the syntheses of other desirable Ce$^{+3}$ derivatives which require anhydrous starting material. The objective is to prepare anhydrous Ce(NO$_3$)$_3$ · NH$_4$NO$_3$ complex. Another objective of the present invention is to provide a convenient process for making this complex which obviates the need for high temperatures and diffcult-to-work-with reagents normally associated with preparation of the anhydrous halides.

DESCRIPTION OF THE INVENTION

Prior to the present invention, dehydration of cerous nitrate hydrates in accordance with procedures known in the art did not yield anhydrous species (Russian Journal of Inorganic Chemistry, November 1965, p. 1373–1377).

The present invention is a convenient procedure for preparing anhydrous cerous nitrate. It comprises treating dried anhydrous ceric hexanitro ammonium complex (also called ceric ammonium nitrate (CAN)) with a suitable reducing agent (ra) whereby Ce$^{+4}$ is reduced to Ce$^{+3}$ under anhydrous conditions. The resulting Ce$^{+3}$ species, a complex of Ce$^{+3}$ nitrate and ammonia nitrate, can be used as a source of anhydrous Ce$^{+3}$ salt.

The invention can be shown by equation A:

(NH$_4$)$_2$Ce(NO$_3$)$_6$+(ra)→Ce(NO$_3$)$_3$2NH$_4$NO$_3$+HNO$_3$+(PrOX)      A.

where (PrOX) denotes the product of oxidation which depends on the nature of the (ra).

Ceric ammonium nitrate (CAN) is a commercial product that can be freed of all water by simple drying in an oven at 105°–120° C. and atmospheric pressure for about 6–12 hours, or under vacuum at lower temperature. According to the present invention, dried CAN, either in solid state or while suspended/dissolved in an appropriate inert solvent, is contacted with the reducing agent.

In one preferred embodiment of the invention, ammonia is chosen as being the most convenient reducing agent because it is economical and yields a simple by-product, nitrogen, in addition to ammonium nitrate.

It is believed that the following reaction takes place:

3(NH$_4$)$_2$Ce(NO$_3$)$_6$+4NH$_3$→3Ce(NO$_3$)$_3$+9NH$_4$NO$_3$+½ N$_2$      Eq.B

Treatment of solid, previously dried CAN, with NH$_3$ can be done in a variety of ways. Contact of CAN with NH$_3$ is maintained for a period of time sufficient to reduce all Ce$^{+4}$ to Ce$^{+3}$. The time necessary to achieve this depends on the mode of contact, granulometry of the CAN, temperature and pressure. Contact of CAN with NH$_3$ can be done at atmospheric pressure while, for instance, stirring the CAN in an atmosphere of NH$_3$. The ammonia can also be maintained under pressure or used as a liquid. When liquid NH$_3$ is used the excess is easily recovered after the reaction has been completed.

The amount of ammonia should at least be stoichiometric but normally larger amounts are employed. The excess of ammonia can be recovered. Small amounts (about 2 mole) of ammonia which remain coordinated to the cerium nitrate complex can ultimately be expelled if desired. The temperature during contact can be as low as the temperature of liquid ammonia or as high as about 130° C., but below the temperature of decomposition of CAN which starts at about 170° C.

CAN can be reduced while in suspension or in solution in inert solvents such as benzene, pentane, petroleum ethers or glymes. The product need not be isolated from the inert solvent. Once complete reduction with NH$_3$ has been achieved, reagents can be added to accomplish subsequent conversion of the anhydrous Ce$^{+3}$ nitrate complex to the desired Ce$^{+3}$ derivative.

While reducing CAN with NH$_3$ is the most efficient and inexpensive way to produce the desired Ce$^{+3}$ nitrate complex, a host of other reducing agents can also be used. The most useful ones, because of their low cost, relative ease to accomplish the reaction and relative ease to remove the (PrOX) if necessary, are the lower alkyl alcohols such as methanol, ethanol, propanol, isopropanol, etc. Generally, the reducing agent suitable for the present invention is one that will react as a reducing agent in anhydrous medium, and lead to substantially complete reduction of Ce$^{+4}$ to Ce$^{+3}$. The number of species that can be used for that purpose is very large indeed. This can be appreciated by citing the case of, dimethoxy ethane, considered an inert solvent which can be made to react with the CAN at reflux temperature totally reducing Ce$^4$ to Ce$^{+3}$. The reduction may proceed fast or slow depending on the reducing agent. It can be speeded up if desired by UV irradiation, heating or adding an appropriate catalyst. During this step of the process, the Ce$^{+4}$ is reduced to Ce$^{+3}$ while the medium remains anhydrous. As shown in the equation A, nitric acid is produced during the reduction and it will remain as such in the mixture if the reduction agent is a neutral species such as alcohol. Besides nitric acid, the mixture will also contain an oxidation (PrOX) by-product.

The amount of (ra) needs to be at least stoichiometric, but in practice excess is used in order to speed up the process of reduction. The nitric acid can be neutralized and the (PrOX) removed from the system in the event the Ce$^{+3}$ nitrate complex is to be isolated.

Efforts to isolate Ce(NO$_3$)$_3$ in a free state did not succeed. Apparently, Ce$^{+3}$ ion needs to be additionally coordinated. In the absence of water or other coordinating agents this is being accomplished by ammonium nitrate. As in the case of CAN and other common examples for lanthanide elements, coordination ligands can be removed in subsequent reactions if desired and do not present a major problem. A certain amount of NH$_3$ also becomes molecularly bonded to the cerium nitrate complex, and in some instances its presence may be desirable. When, for instance, the resulting anhydrous Ce$^{+3}$ product is to be reacted with an alcohol or silanol in the presence of NH$_3$, the coordinated NH$_3$ serves as a portion of the NH$_3$ required. In other cases its presence may not be desirable and steps must be taken to remove it, such as pumping under vacuum, under heating, neutralizing with dry HCl or displacing with another coordinating agent.

The following examples illustrate the invention but should not be interpreted as limiting the scope.

The presence or absence of Ce$^4$ was determined by adding barium diphenylamine sulfate to a sample acidified with glacial acidic acid. When Ce$^4$ is present, the solution shows an intense purple color.

EXAMPLES

EXAMPLE 1

Reduction of CAN with ammonia in pentane:

70.5 g (0.128 mol) of previously dryed CAN (yellow-orange) were suspended in 500 ml pentane. The inert gas atmosphere was exchanged with ammonia and the whole system stirred well for 24 hours. During this time the reacting material turned colorless, indicating completion of the reduction. The suspension was filtered and the new compound dried at high vacuum and used without further purification for subsequent reactions. Yield: 79.4 g of a colorless powder. The product contained coordinated ammonia.

EXAMPLE 2

Reduction of CAN with ammonia in dimethoxyethane:

5 g (9.21 mmol) CAN were dissolved in 60 ml DME, the solution degassed, saturated with ammonia and stirred overnight. By the next morning the suspended solid had completely lost its yellow-orange color.

EXAMPLE 3

Reduction of CAN with ammonia, without solvent:

5 g (9.21 mmol) CAN were efficiently stirred without any solvent in ammonia atmosphere for one week. After this time all the CAN had turned colorless. The cerium-(IV) test was negative.

EXAMPLE 4

3.44 grams CAN with 46.4 grams DME were refluxed overnight. The next day, there was no Ce$^4$ remaining in the flask. The resulting pH was 4.0 indicating that freed HNO$_3$ did react with the oxidation by-products. Also present were nitrous fumes.

EXAMPLE 5

5.0 grams CAN with 50 ml DME were mixed in the presence of 0.4g charcoal catalyst. All Ce$^4$ was reduced in less than 1.5 hours, and final pH was 1.0.

EXAMPLE 6

In argon atmosphere, 5.0 grams CAN with 45.6 g methanol were mixed at room temperature by stirring in the presence of 0.06g Platinum/Carbon catalyst. Complete reduction was achieved in 30 minutes, and final pH was 1.0.

EXAMPLE 7

5 0g CAN, 45 g isopropylalcohol and 0.06 g 5% Ruthenium/Carbon catalyst were stirred at room temperature in an argon atmosphere. Complete reduction of Ce$^4$ was observed in 2 hours.

EXAMPLE 8

2 0g CAN mixed with 20 cc methanol was exposed to sunlight for one day. Complete reduction occurred.

EXAMPLE 9

The procedure described in Example 13 was repeated with the exception that methanol is replaced by isopropanol, and similar results were obtained.

EXAMPLE 10

The procedure described in Example 13 was repeated with the exception that UV light is substituted for sunlight, and similar results were achieved.

EXAMPLE 11

5 0 g CAN, 44.7 g n-butanol and 0.06 g 5% Ruthenium/Carbon catalyst were mixed. Complete reduction was achieved in 2 hours.

EXAMPLE 12

Attempts to isolate non-complexed $Ce(NO_3)_3$:

Fractionating extraction with methanol where $NH_4NO_3$ is sufficiently soluble failed. The $NH_4NO_3$ appeared strongly bonded to the $Ce(NO_3)_3$. Bound ammonia, however, was completely dissociated from the complex during the treatment which left a pure $Ce(NO_3)_3 3NH_4NO_3$ complex.

The same conclusions were reached after an attempt to separate $NH_4NO_3$ by sublimation in high vacuum failed.

EXAMPLE 13

Reaction of cerium (III) nitrate with sodium isopropoxide

To a freshly prepared suspension of cerium (III) nitrate complex (1.85 mmol) in DME were added 11.1 mmol (4.17 ml of a 2.66 molar solution) of NaOiPr in isopropanol. After 2 hours the reaction mixture was filtered, yielding 801 mg $NaNO_3 = 87.3\%$ of the expectec $NaNO_3$ (some solid remained on the walls of the frit). The filtrate was dried, slurried up in pentane and filtered. Yield: 810 mg (1.63 mmol)=88.1% for Ce-$(OiPr)_3(HOiPr)_3$ (M.W.=497.67)

The nmr spectra was essentially identical to the one taken from a compound prepared independently by reaction of $CeCl_3$ with NaOiPr in THF/IPA.

EXAMPLE 14

Preparation of Methoxides and isopropoxides of Ce III

Previously dried CAN is dissolved in excess of methanol and exposed to daylight until all $Ce^4$ is reduced.

An aliquot of the reaction mixture is treated with $NH_3$ gas whereby $Ce(OCH_3)_3$ precipitates. The methoxide is separated from the ammonium nitrate by extraction and washing with methanol or the reaction mixture used without separation in subsequent synthesis.

Another aliquot is subjected to vacuum removal of all excess methanol and acetaldehyde which is a product of the oxidation of methanol by CAN. The remaining solid is mixed with isopropanol and then reacted with sodium isopropoxide to convert the $Ce(NO_3)_3$ to $Ce(OiPr)_3$.

EXAMPLE 15

Reaction of the cerous nitrate complex with triphenylsilanol

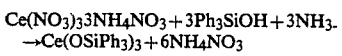

5 g 0.0088m) of $Ce(NO_3)_3 . 3NH_4NO_3$ were suspended in 40 ml (35g) of DME. 7.32 g (0.026 m) of $Ph_3SiOH$ were added as a solid and stirred for five minutes. In the next five minutes $NH_3$ gas was bubbled through the suspension forming a light yellow clear upper phase. Addition of $NH_3$ gas was continued in the next 10 minutes. Subsequent filtration of the mixture using a shlenk frit yielded a clear, light yellow filtrate. After removing the solvent at oil-pump vacuum, 5.8 g of a white powder was obtained. Good solubility in $CHCl_3$, DME, THF.

$^1H$ NMR ($CHCl_3$-d) S 7.24; 7.31; 7.36; 7.49; 7.52; 7.57; 7.59. $^{13}C$ NMR ($CHCl_3$-d) S 127.76; 129.93; 134.91.

EXAMPLE 16

Cerium (III) Alkanolatoamine derivatives

Aliquots of $Ce(NO_3)_3$-$NH_4NO_3$ complex stirred in methanol is combined with various ratios of the following alkanolamines.

monoethanol amine (1:1, 1:2, 1:3)
diethanol amine (1:1, 1:2)
triethanol amine (1:1)
diethanolamine (1:1, 1:2, 1:3).

After the addition of ammonia, the corresponding alkanolatoamines are obtained, via exchange with the $Ce(OCH_3)$, produced in situ.

What is claimed is:

1. A Process for preparing an anhydrous cerous nitrate complex comprising:
   (a) contacting water-free ceric ammonium nitrate with a suitable reducing agent under anhydrous conditions; and
   (b) maintaining contact for a period of time sufficient to reduce cerium (IV) to cerium III and form the anhydrous cerous nitrate complex.
2. A process according to claim 1 wherein the reducing agent is ammonia gas.
3. A process according to claim 2 wherein the ceric ammonium nitrate is in a solid state.
4. A process according to claim 2 wherein the ceric ammonium nitrate is suspended or dissolved in an inert solvent.
5. A process according to claim 2 conducted under about atmospheric pressure.
6. A process according to claim 2 conducted under pressure greater than atmospheric.
7. A Process according to claim 1 conducted under temperature between about 0° and about 100° C.
8. A process according to claim 1 conducted at a temperature less than the decomposition temperature of CAN.
9. A process according to claim 1 where the reducing agent is ammonia in a liquid state.
10. A process according to claim 1 wherein the reducing agent is a lower alkyl alcohol.
11. A process according to claim 10 wherein the alcohol is methanol.
12. A process according to claim 10 wherein the reduction is carried out in the presence of a catalyst.
13. A process according to claim 10 wherein the reduction is carried out under exposure to ultra violet light.
14. A product of claim 1 comprising cerous nitrate-ammonium nitrate-ammonia complex.
15. Anhydrous cerous nitrate-ammonium nitrate-ammonia complex.

* * * * *